ies United States Patent (10) Patent No.: US 11,253,265 B2
Montidoro et al. (45) Date of Patent: Feb. 22, 2022

(54) PULL WIRE DETACHMENT FOR INTRAVASCULAR DEVICES

(71) Applicant: DePuy Synthes Products, Inc., Raynham, MA (US)

(72) Inventors: Tyson Montidoro, Raynham, MA (US); Juan Lorenzo, Raynham, MA (US)

(73) Assignee: DePuy Synthes Products, Inc., Raynham, MA (US)

( * ) Notice: Subject to any disclaimer, the term of this patent is extended or adjusted under 35 U.S.C. 154(b) by 306 days.

(21) Appl. No.: 16/444,659

(22) Filed: Jun. 18, 2019

(65) Prior Publication Data

US 2020/0397444 A1 Dec. 24, 2020

(51) Int. Cl.
*A61B 17/12* (2006.01)
*A61M 25/00* (2006.01)
*A61M 25/06* (2006.01)

(52) U.S. Cl.
CPC ..... *A61B 17/1214* (2013.01); *A61M 25/0074* (2013.01); *A61M 25/0662* (2013.01); *A61B 2017/12054* (2013.01)

(58) Field of Classification Search
CPC .... A61F 2/01; A61F 2/966; A61F 2/95; A61F 2/011; A61F 2002/9511; A61B 17/12109; A61B 17/1214; A61B 2017/12054; A61M 25/0074; A61M 25/0662
See application file for complete search history.

(56) References Cited

U.S. PATENT DOCUMENTS

| 3,429,408 A | 2/1969 | Maker et al. |
| 5,108,407 A | 4/1992 | Geremia et al. |
| 5,122,136 A | 6/1992 | Guglielmi et al. |
| 5,250,071 A | 10/1993 | Palermo |
| 5,263,964 A | 11/1993 | Purdy |

(Continued)

FOREIGN PATENT DOCUMENTS

| EP | 1985244 A2 | 10/2008 |
| EP | 2498691 | 9/2012 |

(Continued)

OTHER PUBLICATIONS

Extended European Search Report dated Nov. 18, 2020 in European Patent Application No. 20178690.

(Continued)

*Primary Examiner* — George J Ulsh
(74) *Attorney, Agent, or Firm* — Troutman Pepper Hamilton Sanders LLP

(57) ABSTRACT

An assembly at a proximal end of an intravascular delivery system can allow the proximal end of a pull wire to move independently of a delivery tube. The assembly can generally include the pull wire, the delivery tube, a feature to prevent the proximal end of the pull wire from becoming inaccessible due to distal movement of the pull wire, and a feature to protect the proximal end of the pull wire from inadvertent, premature manipulation. When the intravascular delivery system is navigating tortuous vasculature, the proximal end of the pull wire can move distally in relation to the proximal end of delivery tube, relieving stress on the distal end of the pull wire. The proximal end of the pull wire can be protected from inadvertent manipulation during delivery and made available for manipulation once the distal end of the delivery system is in place.

12 Claims, 6 Drawing Sheets

(56) References Cited

U.S. PATENT DOCUMENTS

| | | |
|---|---|---|
| 5,334,210 A | 8/1994 | Gianturco |
| 5,350,397 A | 9/1994 | Palermo et al. |
| 5,382,259 A | 1/1995 | Phelps et al. |
| 5,484,409 A | 1/1996 | Atkinson et al. |
| 5,569,221 A | 10/1996 | Houser et al. |
| 5,899,935 A | 5/1999 | Ding |
| 5,925,059 A | 7/1999 | Palermo et al. |
| 6,113,622 A | 9/2000 | Hieshima |
| 6,203,547 B1 | 3/2001 | Nguyen et al. |
| 6,391,037 B1 | 5/2002 | Greenhalgh |
| 6,454,780 B1 | 9/2002 | Wallace |
| 6,506,204 B2 | 1/2003 | Mazzocchi |
| 6,561,988 B1 | 5/2003 | Turturro et al. |
| 7,367,987 B2 | 5/2008 | Balgobin et al. |
| 7,371,251 B2 | 5/2008 | Mitelberg et al. |
| 7,371,252 B2 | 5/2008 | Balgobin et al. |
| 7,377,932 B2 | 5/2008 | Mitelberg et al. |
| 7,708,754 B2 | 5/2010 | Balgobin et al. |
| 7,708,755 B2 | 5/2010 | Davis, III et al. |
| 7,799,052 B2 | 9/2010 | Balgobin et al. |
| 7,811,305 B2 | 10/2010 | Balgobin et al. |
| 7,819,891 B2 | 10/2010 | Balgobin et al. |
| 7,819,892 B2 | 10/2010 | Balgobin et al. |
| 7,901,444 B2 | 3/2011 | Slazas |
| 7,985,238 B2 | 7/2011 | Balgobin et al. |
| 8,062,325 B2 | 11/2011 | Mitelberg et al. |
| 8,333,796 B2 | 12/2012 | Tompkins et al. |
| 9,155,540 B2 | 10/2015 | Lorenzo |
| 9,232,992 B2 | 1/2016 | Heidner |
| 9,314,326 B2 | 4/2016 | Wallace et al. |
| 9,532,792 B2 | 1/2017 | Galdonik et al. |
| 9,532,873 B2 | 1/2017 | Kelley |
| 9,533,344 B2 | 1/2017 | Monetti et al. |
| 9,539,011 B2 | 1/2017 | Chen et al. |
| 9,539,022 B2 | 1/2017 | Bowman |
| 9,539,122 B2 | 1/2017 | Burke et al. |
| 9,539,382 B2 | 1/2017 | Nelson |
| 9,549,830 B2 | 1/2017 | Bruszewski et al. |
| 9,554,805 B2 | 1/2017 | Tompkins et al. |
| 9,561,125 B2 | 2/2017 | Bowman et al. |
| 9,572,982 B2 | 2/2017 | Burnes et al. |
| 9,579,484 B2 | 2/2017 | Barnell |
| 9,585,642 B2 | 3/2017 | Dinsmoor et al. |
| 9,615,832 B2 | 4/2017 | Bose et al. |
| 9,615,951 B2 | 4/2017 | Bennett et al. |
| 9,622,753 B2 | 4/2017 | Cox |
| 9,636,115 B2 | 5/2017 | Henry et al. |
| 9,636,439 B2 | 5/2017 | Chu et al. |
| 9,642,675 B2 | 5/2017 | Werneth et al. |
| 9,655,633 B2 | 5/2017 | Leynov et al. |
| 9,655,645 B2 | 5/2017 | Staunton |
| 9,655,989 B2 | 5/2017 | Cruise et al. |
| 9,662,120 B2 | 5/2017 | Lagodzki et al. |
| 9,662,129 B2 | 5/2017 | Galdonik et al. |
| 9,662,238 B2 | 5/2017 | Dwork et al. |
| 9,662,425 B2 | 5/2017 | Lilja et al. |
| 9,668,898 B2 | 6/2017 | Wong |
| 9,675,477 B2 | 6/2017 | Thompson |
| 9,675,782 B2 | 6/2017 | Connolly |
| 9,676,022 B2 | 6/2017 | Ensign et al. |
| 9,692,557 B2 | 6/2017 | Murphy |
| 9,693,852 B2 | 7/2017 | Lam et al. |
| 9,700,262 B2 | 7/2017 | Janik et al. |
| 9,700,399 B2 | 7/2017 | Acosta-Acevedo |
| 9,717,421 B2 | 8/2017 | Griswold et al. |
| 9,717,500 B2 | 8/2017 | Tieu et al. |
| 9,717,502 B2 | 8/2017 | Teoh et al. |
| 9,724,103 B2 | 8/2017 | Cruise et al. |
| 9,724,526 B2 | 8/2017 | Strother et al. |
| 9,750,565 B2 | 9/2017 | Bloom et al. |
| 9,757,260 B2 | 9/2017 | Greenan |
| 9,764,111 B2 | 9/2017 | Gulachenski |
| 9,770,251 B2 | 9/2017 | Bowman |
| 9,770,577 B2 | 9/2017 | Li |
| 9,775,621 B2 | 10/2017 | Tompkins et al. |
| 9,775,706 B2 | 10/2017 | Paterson |
| 9,775,732 B2 | 10/2017 | Khenansho |
| 9,788,800 B2 | 10/2017 | Mayoras, Jr. |
| 9,795,391 B2 | 10/2017 | Saatchi et al. |
| 9,801,980 B2 | 10/2017 | Karino et al. |
| 9,808,599 B2 | 11/2017 | Bowman et al. |
| 9,833,252 B2 | 12/2017 | Sepetka et al. |
| 9,833,604 B2 | 12/2017 | Lam et al. |
| 9,833,625 B2 | 12/2017 | Waldhauser et al. |
| 9,918,718 B2 | 3/2018 | Lorenzo |
| 10,285,710 B2 | 5/2019 | Lorenzo et al. |
| 10,292,851 B2 | 5/2019 | Gorochow |
| 10,517,604 B2 | 12/2019 | Bowman et al. |
| 10,806,402 B2 | 10/2020 | Cadieu et al. |
| 10,806,461 B2 | 10/2020 | Lorenzo |
| 2001/0049519 A1 | 12/2001 | Holman et al. |
| 2002/0072705 A1 | 6/2002 | Vrba et al. |
| 2002/0165569 A1 | 11/2002 | Ramzipoor et al. |
| 2004/0034363 A1 | 2/2004 | Wilson et al. |
| 2004/0059367 A1 | 3/2004 | Davis et al. |
| 2004/0087964 A1 | 5/2004 | Diaz et al. |
| 2006/0025801 A1 | 2/2006 | Lulo et al. |
| 2006/0064151 A1 | 3/2006 | Guterman |
| 2006/0116711 A1 | 6/2006 | Elliott et al. |
| 2006/0116714 A1 | 6/2006 | Sepetka et al. |
| 2006/0135986 A1 | 6/2006 | Wallace et al. |
| 2006/0206139 A1 | 9/2006 | Tekulve |
| 2006/0247677 A1 | 11/2006 | Cheng et al. |
| 2006/0276824 A1 | 12/2006 | Mitelberg et al. |
| 2006/0276825 A1 | 12/2006 | Mitelberg et al. |
| 2006/0276826 A1 | 12/2006 | Mitelberg et al. |
| 2006/0276827 A1 | 12/2006 | Mitelberg et al. |
| 2006/0276830 A1 | 12/2006 | Balgobin et al. |
| 2006/0276833 A1 | 12/2006 | Balgobin et al. |
| 2007/0010850 A1 | 1/2007 | Balgobin et al. |
| 2007/0055302 A1 | 3/2007 | Henry et al. |
| 2007/0083132 A1 | 4/2007 | Sharrow |
| 2007/0233168 A1 | 10/2007 | Davis et al. |
| 2007/0270903 A1 | 11/2007 | Davis, III et al. |
| 2008/0027561 A1 | 1/2008 | Mitelberg et al. |
| 2008/0045997 A1 | 2/2008 | Balgobin et al. |
| 2008/0097462 A1 | 4/2008 | Mitelberg et al. |
| 2008/0281350 A1 | 11/2008 | Sepetka |
| 2008/0300616 A1 | 12/2008 | Que et al. |
| 2008/0306503 A1 | 12/2008 | Que et al. |
| 2009/0062726 A1 | 3/2009 | Ford et al. |
| 2009/0312748 A1 | 12/2009 | Johnson et al. |
| 2010/0114017 A1 | 5/2010 | Lenker et al. |
| 2010/0324649 A1 | 12/2010 | Mattsson |
| 2011/0202085 A1 | 8/2011 | Loganathan et al. |
| 2011/0295303 A1 | 12/2011 | Freudenthal |
| 2012/0035707 A1 | 2/2012 | Mitelberg et al. |
| 2012/0041472 A1 | 2/2012 | Tan et al. |
| 2012/0283768 A1 | 11/2012 | Cox et al. |
| 2013/0066413 A1 | 3/2013 | Jin et al. |
| 2014/0058435 A1 | 2/2014 | Jones et al. |
| 2014/0135812 A1 | 5/2014 | Divino et al. |
| 2014/0200607 A1 | 7/2014 | Sepetka et al. |
| 2014/0277084 A1 | 9/2014 | Mirigian et al. |
| 2014/0277085 A1 | 9/2014 | Mirigian et al. |
| 2014/0277092 A1 | 9/2014 | Teoh et al. |
| 2014/0277093 A1 | 9/2014 | Guo et al. |
| 2015/0005808 A1 | 1/2015 | Chouinard et al. |
| 2015/0182227 A1 | 7/2015 | Le et al. |
| 2015/0230802 A1 | 8/2015 | Lagodzki et al. |
| 2015/0335333 A1 | 11/2015 | Jones et al. |
| 2016/0008003 A1 | 1/2016 | Kleshinski et al. |
| 2016/0022275 A1 | 1/2016 | Garza |
| 2016/0157869 A1 | 6/2016 | Elgard et al. |
| 2016/0228125 A1 | 8/2016 | Pederson, Jr. et al. |
| 2016/0310304 A1 | 10/2016 | Mialhe |
| 2016/0346508 A1 | 12/2016 | Williams et al. |
| 2017/0007264 A1 | 1/2017 | Cruise et al. |
| 2017/0007265 A1 | 1/2017 | Guo et al. |
| 2017/0020670 A1 | 1/2017 | Murray et al. |
| 2017/0020700 A1 | 1/2017 | Bienvenu et al. |
| 2017/0027640 A1 | 2/2017 | Kunis et al. |
| 2017/0027692 A1 | 2/2017 | Bonhoeffer |
| 2017/0027725 A1 | 2/2017 | Argentine |

(56) References Cited

U.S. PATENT DOCUMENTS

| | | |
|---|---|---|
| 2017/0035436 A1 | 2/2017 | Morita |
| 2017/0035567 A1 | 2/2017 | Duffy |
| 2017/0042548 A1 | 2/2017 | Lam |
| 2017/0049596 A1 | 2/2017 | Schabert |
| 2017/0071737 A1 | 3/2017 | Kelley |
| 2017/0072452 A1 | 3/2017 | Monetti et al. |
| 2017/0079671 A1 | 3/2017 | Morero et al. |
| 2017/0079680 A1 | 3/2017 | Bowman |
| 2017/0079766 A1 | 3/2017 | Wang et al. |
| 2017/0079767 A1 | 3/2017 | Leon-Yip |
| 2017/0079812 A1 | 3/2017 | Lam et al. |
| 2017/0079817 A1 | 3/2017 | Sepetka et al. |
| 2017/0079819 A1 | 3/2017 | Pung et al. |
| 2017/0079820 A1 | 3/2017 | Lam et al. |
| 2017/0086851 A1 | 3/2017 | Wallace et al. |
| 2017/0086996 A1 | 3/2017 | Peterson et al. |
| 2017/0095258 A1 | 4/2017 | Tassoni et al. |
| 2017/0095259 A1 | 4/2017 | Tompkins et al. |
| 2017/0100126 A1 | 4/2017 | Bowman et al. |
| 2017/0100141 A1 | 4/2017 | Morero et al. |
| 2017/0100143 A1 | 4/2017 | Granfield |
| 2017/0100183 A1 | 4/2017 | Iaizzo et al. |
| 2017/0113023 A1 | 4/2017 | Steingisser et al. |
| 2017/0147765 A1 | 5/2017 | Mehta |
| 2017/0151032 A1 | 6/2017 | Loisel |
| 2017/0165062 A1 | 6/2017 | Rothstein |
| 2017/0165065 A1 | 6/2017 | Rothstein et al. |
| 2017/0165454 A1 | 6/2017 | Tuohy |
| 2017/0172581 A1 | 6/2017 | Bose et al. |
| 2017/0172766 A1 | 6/2017 | Vong et al. |
| 2017/0172772 A1 | 6/2017 | Khenansho |
| 2017/0189033 A1 | 7/2017 | Sepetka et al. |
| 2017/0189035 A1 | 7/2017 | Porter |
| 2017/0215902 A1 | 8/2017 | Leynov et al. |
| 2017/0216484 A1 | 8/2017 | Cruise et al. |
| 2017/0224350 A1 | 8/2017 | Shimizu et al. |
| 2017/0224355 A1 | 8/2017 | Bowman et al. |
| 2017/0224467 A1 | 8/2017 | Piccagli et al. |
| 2017/0224511 A1 | 8/2017 | Dwork et al. |
| 2017/0224953 A1 | 8/2017 | Tran et al. |
| 2017/0231749 A1 | 8/2017 | Perkins et al. |
| 2017/0245864 A1 | 8/2017 | Franano et al. |
| 2017/0245885 A1 | 8/2017 | Lenker |
| 2017/0252064 A1 | 9/2017 | Staunton |
| 2017/0258476 A1 | 9/2017 | Hayakawa et al. |
| 2017/0265983 A1 | 9/2017 | Lam et al. |
| 2017/0281192 A1 | 10/2017 | Tieu et al. |
| 2017/0281331 A1 | 10/2017 | Perkins et al. |
| 2017/0281344 A1 | 10/2017 | Costello |
| 2017/0281909 A1 | 10/2017 | Northrop et al. |
| 2017/0281912 A1 | 10/2017 | Melder |
| 2017/0290593 A1 | 10/2017 | Cruise et al. |
| 2017/0290654 A1 | 10/2017 | Sethna |
| 2017/0296324 A1 | 10/2017 | Argentine |
| 2017/0296325 A1 | 10/2017 | Marrocco et al. |
| 2017/0303939 A1 | 10/2017 | Greenhalgh et al. |
| 2017/0303942 A1 | 10/2017 | Greenhalgh et al. |
| 2017/0303947 A1 | 10/2017 | Greenhalgh et al. |
| 2017/0303948 A1 | 10/2017 | Wallace et al. |
| 2017/0304041 A1 | 10/2017 | Argentine |
| 2017/0304097 A1 | 10/2017 | Corwin et al. |
| 2017/0304595 A1 | 10/2017 | Nagasrinivasa et al. |
| 2017/0312109 A1 | 11/2017 | Le |
| 2017/0312484 A1 | 11/2017 | Shipley et al. |
| 2017/0316561 A1 | 11/2017 | Helm et al. |
| 2017/0319826 A1 | 11/2017 | Bowman et al. |
| 2017/0333228 A1 | 11/2017 | Orth et al. |
| 2017/0333236 A1 | 11/2017 | Greenan |
| 2017/0333678 A1 | 11/2017 | Bowman et al. |
| 2017/0340383 A1 | 11/2017 | Bloom et al. |
| 2017/0348014 A1 | 12/2017 | Wallace et al. |
| 2017/0348514 A1 | 12/2017 | Guyon et al. |
| 2017/0367712 A1 | 12/2017 | Johnson et al. |
| 2018/0028779 A1 | 2/2018 | Oepen et al. |
| 2018/0036508 A1 | 2/2018 | Ozasa et al. |
| 2018/0228493 A1 | 8/2018 | Aguilar et al. |
| 2018/0250150 A1 | 9/2018 | Majercak et al. |
| 2018/0280667 A1 | 10/2018 | Keren |
| 2018/0325706 A1 | 11/2018 | Hebert et al. |
| 2019/0159784 A1 | 5/2019 | Sananes et al. |
| 2019/0192162 A1 | 6/2019 | Lorenzo et al. |
| 2019/0255290 A1 | 8/2019 | Snyder et al. |
| 2019/0314033 A1 | 10/2019 | Mirigian et al. |
| 2019/0328398 A1 | 10/2019 | Lorenzo |
| 2020/0138448 A1 | 5/2020 | Dasnurkar et al. |
| 2020/0187951 A1 | 6/2020 | Blumenstyk |
| 2021/0001082 A1 | 1/2021 | Lorenzo et al. |

FOREIGN PATENT DOCUMENTS

| | | |
|---|---|---|
| EP | 3092956 A1 | 11/2016 |
| EP | 3501427 A1 | 6/2019 |
| JP | 2006-334408 A | 12/2006 |
| JP | 2012-523943 A | 10/2012 |
| JP | 2013-78584 A | 5/2013 |
| WO | WO 2009/132045 A2 | 10/2009 |
| WO | WO 2012/158152 A1 | 11/2012 |
| WO | WO 2017/066386 A1 | 4/2017 |
| WO | WO 2018/022186 A1 | 2/2018 |

OTHER PUBLICATIONS

Extended European Search Report dated Dec. 18, 2020 in European Patent Application No. 20181340.

Extended European Search Report issued in corresponding European Patent Application No. 20 21 2970 dated May 28, 2021.

Extended European Search Report issued in European Patent Application No. 21 15 6857 dated Jun. 22, 2021.

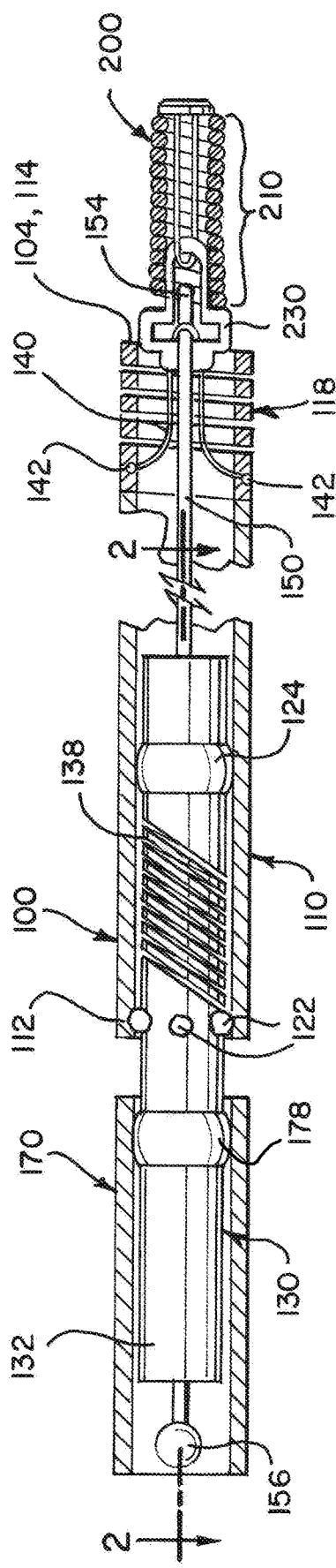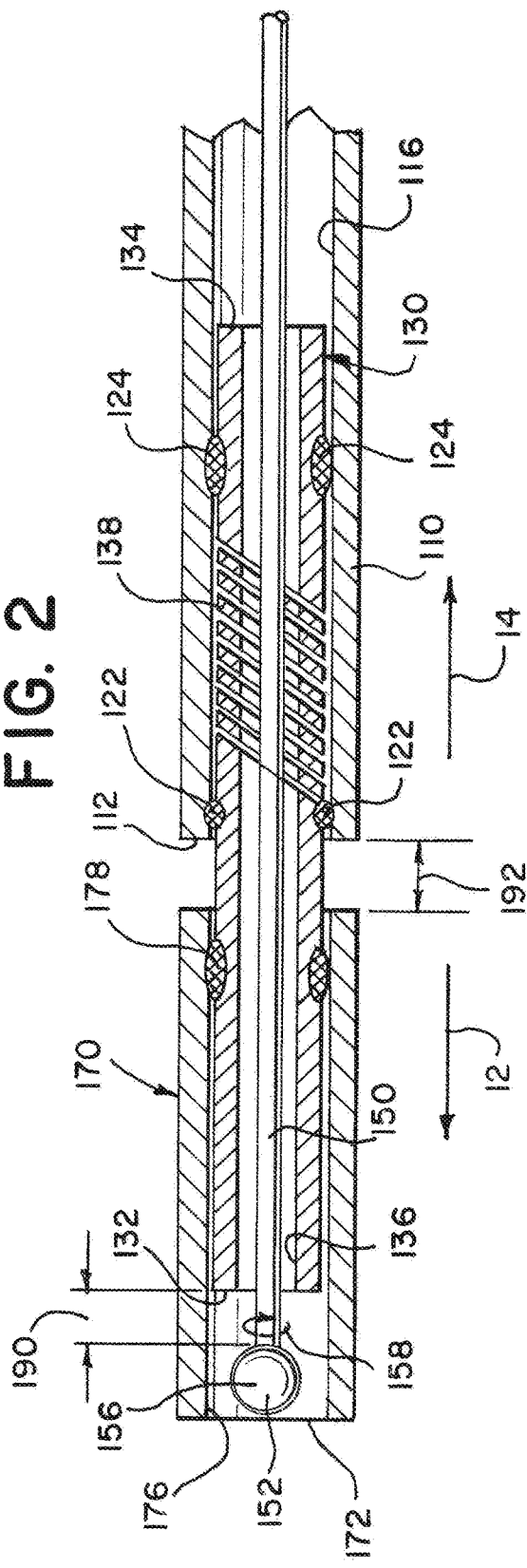

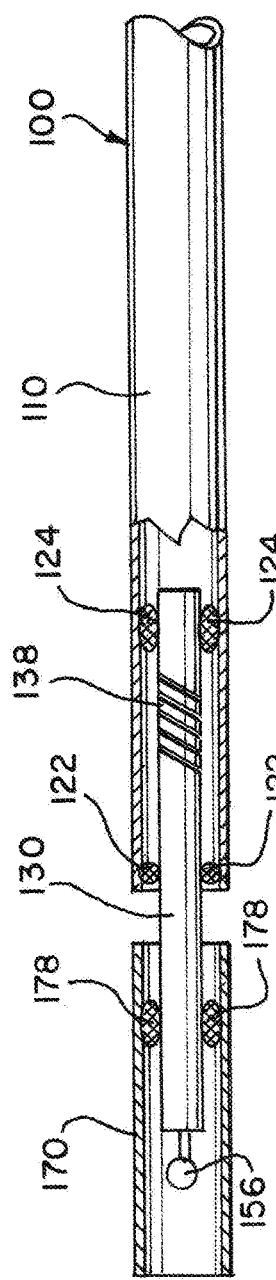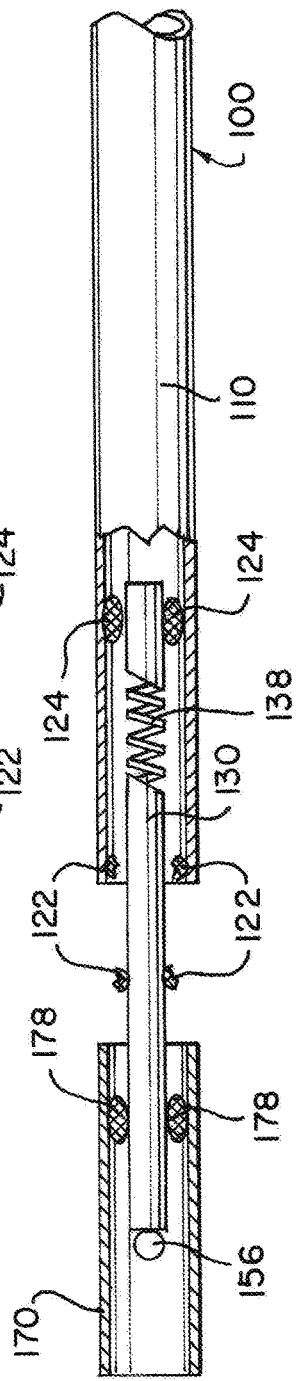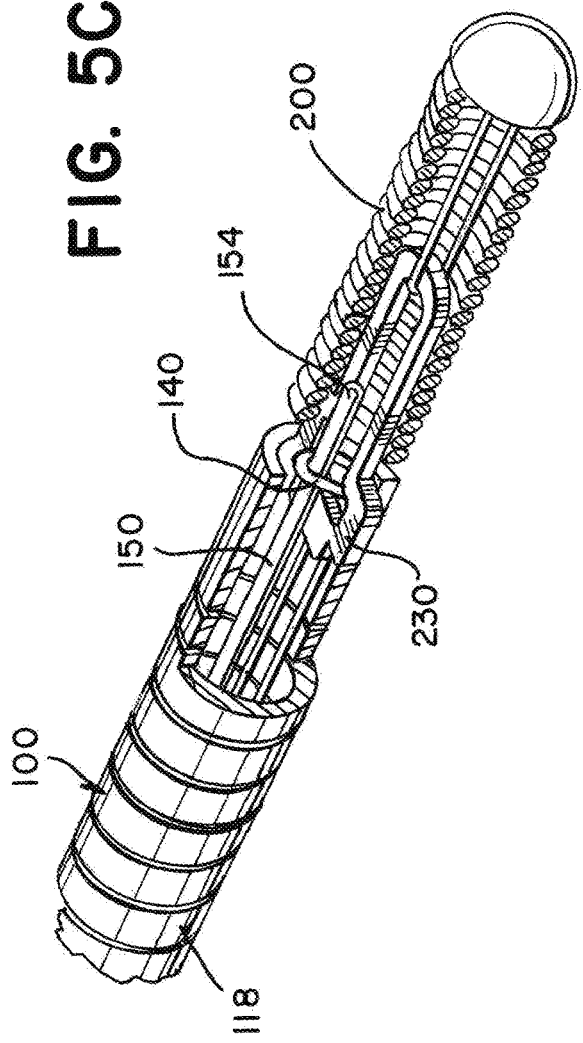

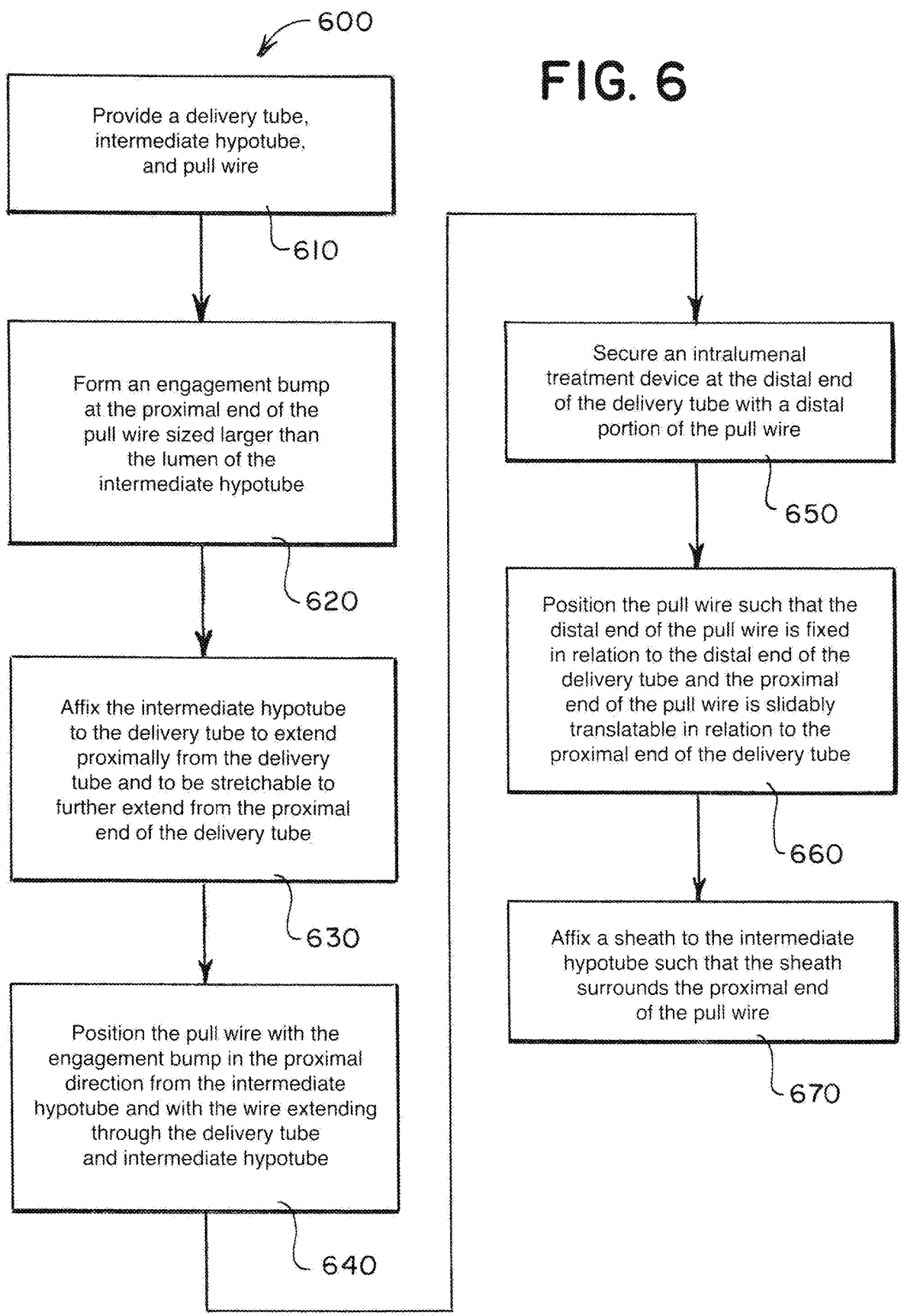

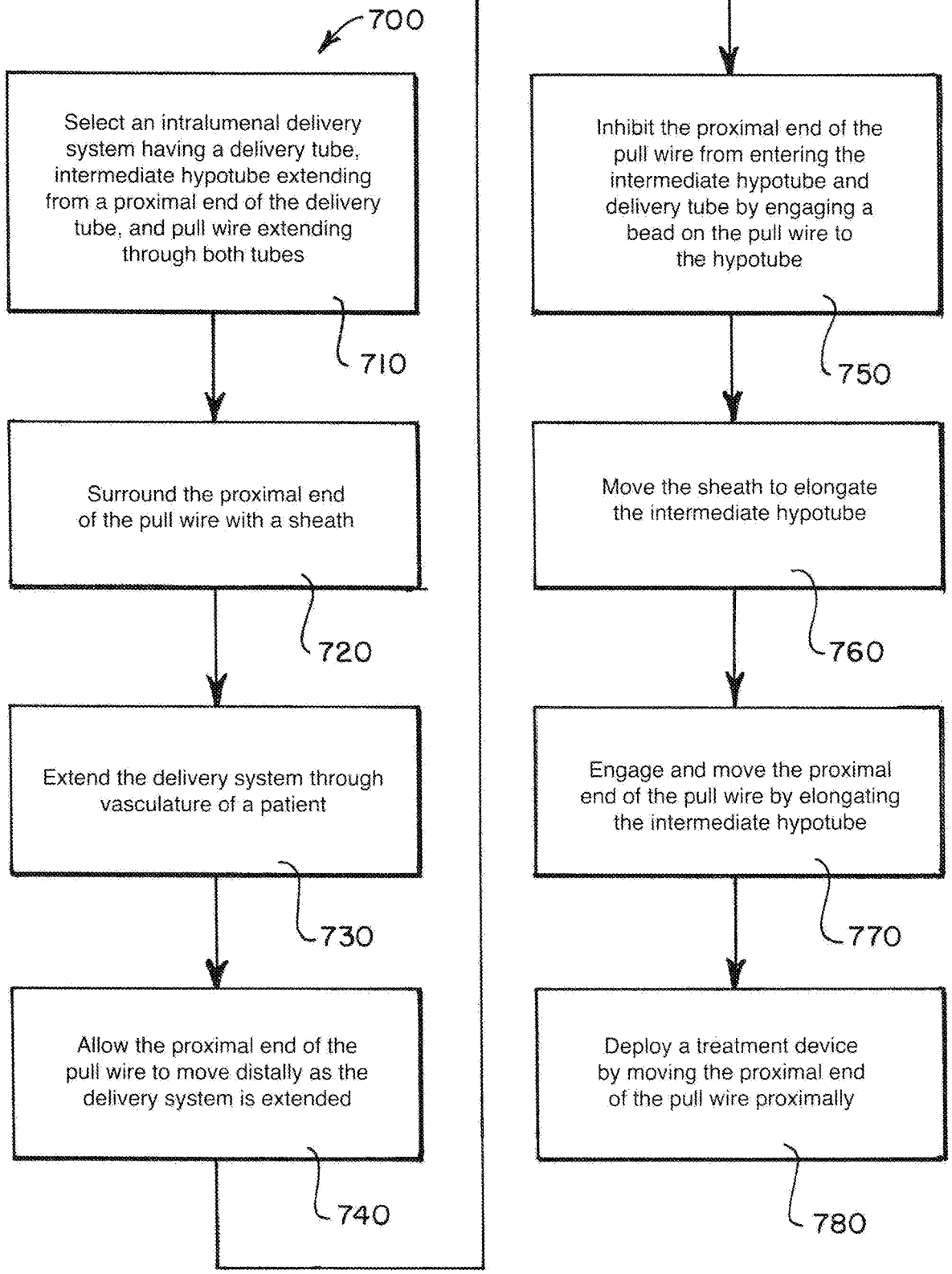

PULL WIRE DETACHMENT FOR INTRAVASCULAR DEVICES

FIELD OF INVENTION

The present invention generally relates to medical devices, and more particularly, to deploying intravascular implants.

BACKGROUND

Numerous intravascular implant devices and clot capture devices are known in the field. Many are deployed and manipulated mechanically, via systems that combine one or more catheters and wires for delivery. Examples of implants that can be delivered mechanically include embolic elements, stents, grafts, drug delivery implants, flow diverters, filters, stimulation leads, sensing leads, or other implantable structures delivered through a microcatheter. Some obstetric and gastrointestinal implants can also be implanted via similar systems that combine one or more catheters and wires. Devices that can be released, deployed, or otherwise manipulated by mechanical means vary greatly in design but can employ a similar delivery catheter and wire system.

Many such catheter-based implant delivery systems include an inner elongated member (or members) extending through the catheter that can be manipulated at the proximal end by a physician to deploy the implant. The inner elongated member(s) can retain the implant in the catheter until the time for release of the implant. These systems can be actuated by retracting or pulling one or more of the inner elongated member(s) relative to the catheter. Such a wire or inner elongated member is referred to herein generically as a "pull wire".

Prematurely release of an implant while tracing through vasculature or before implantation is completed can lead to complications. Mitigating the likelihood of premature release can come at a cost of a less flexible mechanical release system. For instance, when delivering an embolic coil using a release system as described in U.S. Pat. No. 8,062,325 or as described in U.S. patent application Ser. No. 15/964,857, each incorporated herein by reference, it can be desirable to have a minimum length of pull wire extending within the embolic coil in order to minimize stiffening of the proximal end of the coil, however, this limited engagement can result in premature detachment of the coil if significant proximal movement of the pull wire occurs while tracking the delivery system through vasculature.

There is therefore a need for systems, devices, and methods that can mitigate the likelihood of premature deployment of an intravascular treatment device while also providing a flexible mechanical release system.

SUMMARY

It is an object of the present invention to provide systems, devices, and methods to meet the above-stated needs. Generally, it is an object of the present invention to provide an intravascular delivery system having an assembly at its proximal end that allows the proximal end of a pull wire to move independently of a delivery tube and methods for using and making the same to meet the above-stated needs. The assembly can generally include the pull wire, the delivery tube, a feature to prevent the proximal end of the pull wire from becoming inaccessible due to distal movement of the pull wire, and a feature to protect the proximal end of the pull wire from inadvertent, premature manipulation. When the intravascular delivery system is navigating tortuous vasculature, the proximal end of the pull wire can move distally in relation to the proximal end of delivery tube, relieving stress on the distal end of the pull wire. The proximal end of the pull wire can be protected from inadvertent manipulation during delivery and made available for manipulation once the distal end of the delivery system is in place.

In some examples, the feature preventing the proximal end of the pull wire from becoming inaccessible can include a combination of a bump positioned on the proximal end of the pull wire and an intermediate hypotube extending from the proximal end of the delivery tube and providing an engagement surface sized to inhibit the bump from entering the intermediate hypotube. The proximal end of the pull wire can thereby be free to move proximally and/or distally in relation to the hypotube, except when the bump is engaged to the engagement surface of the intermediate hypotube, in which case distal movement of the pull wire is inhibited.

In some examples, the intermediate hypotube can be stretchable. In such examples, the feature protecting the proximal end of the pull wire from inadvertent manipulation can include a breakable attachment that prevents the intermediate hypotube from stretching during delivery of the intravascular treatment device. To deploy the intravascular treatment device, the breakable attachment can be broken, the intermediate hypotube can be stretched, upon stretching, the proximal end of the pull wire can engage the intermediate hypotube, and upon further stretching, the proximal end of the pull wire can be moved in the proximal direction. Sufficient movement of the proximal end of the pull wire can result in proximal translation of the distal end of the pull wire. Sufficient proximal translation of the distal end of the pull wire can result in deployment of the intravascular treatment device.

In some examples, the feature protecting the proximal end of the pull wire from inadvertent manipulation can include a sheath that surrounds the proximal end of the pull wire. The sheath can be affixed to the intermediate hypotube and positioned to surround the proximal end of the pull wire. To deploy the intravascular treatment device, the sheath can be grasped and pulled in the proximal direction in relation to the delivery tube, causing the intermediate hypotube to stretch, and thereby causing the pull wire to engage the intermediate hypotube and translate in the proximal direction.

According to the present invention, an example intravascular delivery system can include a delivery tube, intermediate hypotube, and a pull wire. The intravascular device can be suitable for delivering an intravascular treatment device through patient vascular to a treatment site. To that end, the delivery tube can be sized to be delivered through a patent to a treatment site. During treatment, the intermediate hypotube can be positioned outside of the patent and need not be suitable for entering patent vasculature.

The intermediate hypotube can be affixed to the delivery tube and can extend in the proximal direction from the proximal end of the delivery tube. The pull wire can extend through the lumens of both the intermediate hypotube and the delivery tube. An engagement bump can be affixed to the pull wire and positioned in the proximal direction in relation to the intermediate hypotube proximal end.

The intravascular delivery system can further include a sheath attached to the intermediate hypotube. The sheath can surround the engagement bump and a proximal portion of the pull wire.

The engagement bump can be movable in the distal direction in relation to the proximal end of the intermediate hypotube. A stretch relief gap between the engagement bump and the intermediate hypotube can define a length of travel that the engagement bump can move in the distal direction before engaging the intermediate hypotube.

An intravascular treatment device can be positioned at the distal end of the intravascular delivery system. The pull wire can be movable to deploy the intravascular treatment device.

The distal end of the intermediate hypotube can be positioned within the lumen of the delivery tube. The intermediate hypotube can include an extendable section. The extendable section can be positioned within the lumen of the delivery tube.

An example method for assembling an intravascular delivery system can include one or more of the following steps presented in no particular order, and the method can include additional steps not included here. A delivery tube, intermediate hypotube, and pull wire can be provided. The delivery tube can be sized for delivery through patent vasculature. Both the provided delivery tube and intermediate hypotube can have a respective lumen therethrough.

The intermediate hypotube can be affixed to the delivery tube such that the intermediate hypotube extends in the proximal direction from the proximal end of the delivery tube.

To affix the intermediate hypotube to the delivery tube, a distal end of the intermediate hypotube can be affixed within the lumen of the delivery tube.

The intermediate hypotube can be provided with a strain relief section. To affix the intermediate hypotube to the delivery tube, the strain relief section can be positioned within the lumen of the delivery tube, a portion of the intermediate hypotube in the distal direction from the strain relief section can be affixed to the intermediate hypotube, and a portion of the intermediate hypotube in the proximal direction from the strain relief section can be detachably attached to the delivery tube.

An engagement bump can be formed at the proximal end of the pull wire. The pull wire can be positioned such that the engagement bump is in the proximal direction in relation to the proximal end of the intermediate hypotube and the length of the pull wire extends through the lumens of the intermediate hypotube and the delivery tube. The engagement bump can be sized to inhibit movement of the engagement bump into the lumen of the intermediate hypotube.

The pull wire can be positioned such that the distal end of the pull wire is fixed in relation to the distal end of the delivery tube and the proximal end of the pull wire is slidably translatable in relation to the proximal end of the delivery tube. The distal end of the pull wire can be positioned to secure an intravascular treatment device at the distal end of the delivery tube.

A stretch relief gap can be provided such that the stretch relief gap defines a length over which the engagement bump can move in the distal direction in relation to the intermediate hypotube without engaging the intermediate hypotube.

A sheath having a lumen therethrough can also be provided. The sheath can be affixed to the intermediate hypotube. The engagement bump can be positioned within the lumen of the sheath.

An example method for deploying an intravascular treatment device can include one or more of the following steps presented in no particular order, and the method can include additional steps not included here. An intravascular delivery system can be selected such that the selected delivery system includes a delivery tube, an intermediate hypotube extending from the proximal end of the delivery tube, and a pull wire extending through the lumens of the delivery tube and the intermediate hypotube. The intravascular delivery system can be extended through vasculature of a patient. As the delivery system is extended through the patient, the proximal end of the pull wire can be allowed to move in the distal direction in relation to the proximal end of the delivery tube. The intravascular treatment device can be deployed by moving the proximal end of the pull wire in the proximal direction in relation to the proximal end of the delivery tube.

The pull wire can have a bead positioned at or near the proximal end of the pull wire, and the bead can be engaged to the proximal end of the intermediate hypotube, thereby inhibiting the proximal end of the pull wire from entering the lumen of the intermediate hypotube.

The proximal end of the pull wire can be surrounded by a sheath. To deploy the intravascular treatment device, the sheath can be moved in the proximal direction in relation to the delivery tube. Movement of the sheath can cause the intermediate hypotube to elongate. Elongation of the intermediate hypotube can cause the proximal end of the pull wire to be engaged to the intermediate hypotube. The proximal end of the pull wire can be moved in the proximal direction in relation to the proximal end of the delivery tube by elongating the intermediate hypotube while the proximal end of the pull wire is engaged to the intermediate hypotube.

BRIEF DESCRIPTION OF THE DRAWINGS

The above and further aspects of this invention are further discussed with reference to the following description in conjunction with the accompanying drawings, in which like numerals indicate like structural elements and features in various figures. The drawings are not necessarily to scale, emphasis instead being placed upon illustrating principles of the invention. The figures depict one or more implementations of the inventive devices, by way of example only, not by way of limitation.

FIG. 1 is an illustration of an intravascular delivery system and intravascular implant according to aspects of the present invention;

FIG. 2 is an illustration of a proximal assembly of the intravascular delivery system as indicated in FIG. 1 according to aspects of the present invention;

FIGS. 5A and 5B are illustrations of a proximal assembly of an intravascular delivery system being manipulated for deployment of a treatment device according to aspects of the present invention;

FIG. 5C is an illustration of an intravascular delivery system deploying an implant in response to manipulation of the proximal assembly similar to as illustrated in FIGS. 5A and 5B according to aspects of the present invention;

FIG. 6 is a flow chart outlining method steps for designing and/or constructing a delivery system according to aspects of the present invention; and FIG. 7 is a flow chart outlining method steps for treating a patient using an intravascular delivery system according to aspects of the present invention.

DETAILED DESCRIPTION

Figure 3:
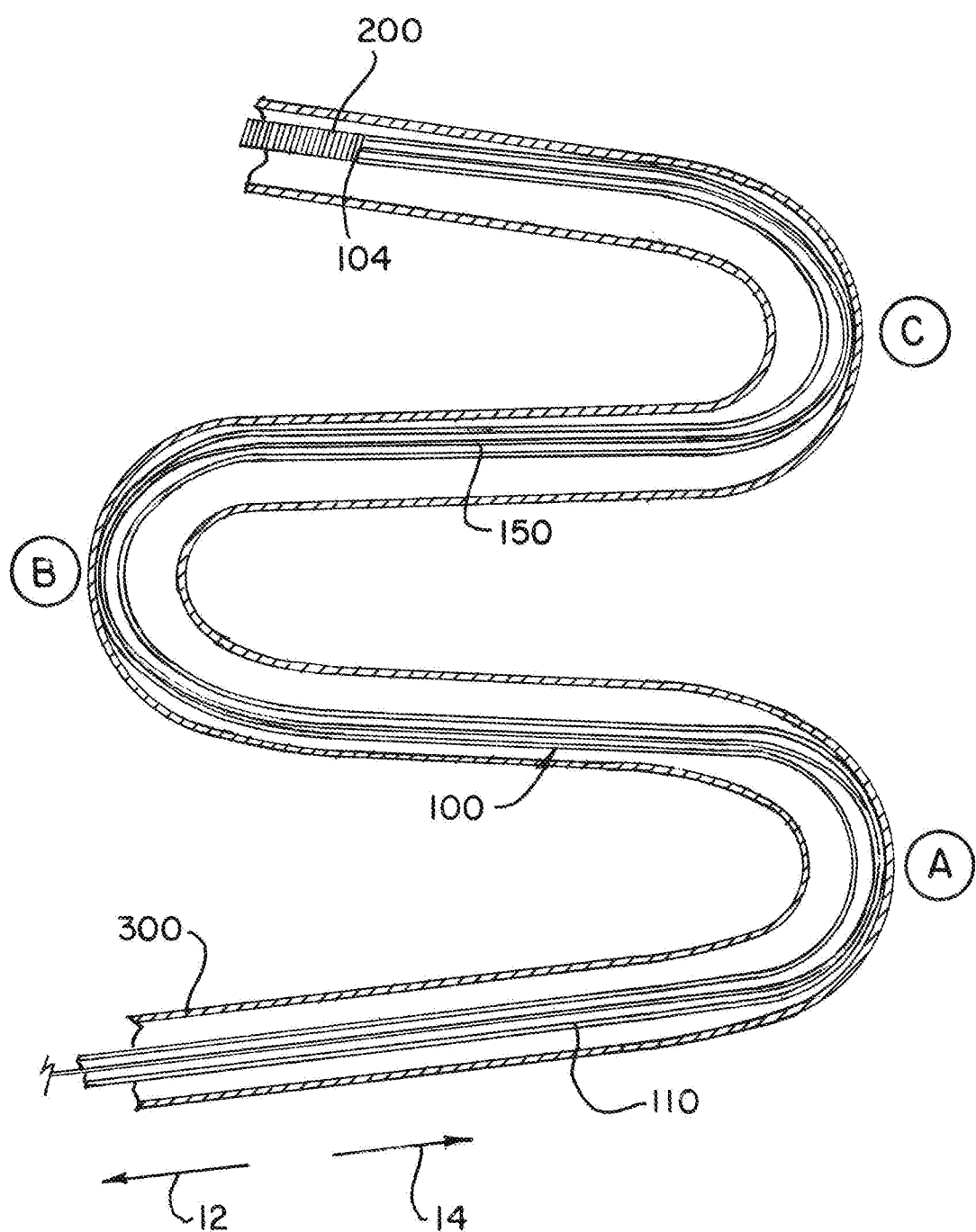
FIG. 3 is an illustration of a delivery system navigating a body lumen according to aspects of the present invention.

In at least some known intravascular delivery systems having a retractable pull wire, the proximal end of the pull wire is substantially fixed in relation to the proximal end of a delivery tube, the distal end of the pull wire is attached to a treatment device deployment system, and a majority of the length of the pull wire is free to move within the confines of the lumen of the delivery tube. When such a delivery system navigates tortuous anatomy, the length of the pull wire can tend to extend to the outer curves of the lumen of the delivery tube, thereby creating a strain force on the attached proximal and distal ends of the pull wire. If the proximal end of the pull wire is securely fixed in relation to the delivery tube, the strain can cause the distal end of the pull wire to move proximally. Significant proximal movement of the distal end of the pull wire can cause the implant or treatment device to deploy prematurely.

In examples presented herein, a slack mechanism can be built on the proximal end of an intravascular delivery system to allow the proximal end of the pull wire to move more freely compared to the distal end of the pull wire. When an example delivery system navigates tortuous anatomy, the proximal end of the pull wire can move distally in relation to the proximal end of the delivery tube to alleviate strain at the distal end of the pull wire, thereby reducing the likelihood that the implant or treatment device is deployed prematurely compared to existing intravascular delivery systems.

The figures illustrate a generally hollow or tubular structures according to the present invention. When used herein, the terms "tubular" and "tube" are to be construed broadly and are not limited to a structure that is a right cylinder or strictly circumferential in cross-section or of a uniform cross-section throughout its length. For example, the tubular structure or system is generally illustrated as a substantially right cylindrical structure. However, the tubular system may have a tapered or curved outer surface without departing from the scope of the present invention.

FIG. 1 is an illustration of an example intravascular delivery system 100. The system can include an assembly at its proximal end for providing strain relief at a distal end 154 of the pull wire 150. The assembly is illustrated in greater detail in FIG. 2. The delivery system 100 can include a delivery tube 110, a loop wire 140 attached to the delivery tube 110 near the distal end 114 of the delivery tube 110, an intermediate hypotube 130 extending from a proximal end 112 of the delivery tube 110, and the pull wire 150. The delivery system 100 can secure an intravascular treatment device 200 such as an embolic coil 210 at the distal end 104 of the delivery system 100 for delivery to a treatment site, and the delivery system 100 can deploy the intravascular treatment device 200 by pulling the pull wire 150 proximally. In FIG. 1, the delivery tube 110 is shown in cross-section. In FIG. 2 the delivery tube 110 and intermediate hypotube 130 are shown in cross-section.

The treatment device 200 can include an engagement feature 230 such as a key. The engagement feature can include an opening positioned at a proximal end of the treatment device 200. The treatment device 200 can be secured to the delivery system 100 by feeding a portion of the loop wire 140 through the opening of the engagement feature 230 and extending the distal end 154 of the pull wire 150 through the loop wire 140.

To deploy the treatment device 200, the pull wire 150 can be pulled proximally such that the distal end 154 of the pull wire passes out of the opening in the loop wire 140, thereby disengaging the loop wire 140. Once the loop wire 140 is disengaged from the pull wire 150, the loop wire 140 can be free to exit the opening in the engagement feature 230.

The delivery tube 110 can include a compressible section 118. The compressible section 118 can be under compression such that once the loop wire 140 is disengaged, the compressible section 118 can decompress, providing a force distally against the treatment device 200. The loop wire 140 can have sufficient flexibility such that when the force is provided from the decompressing compressible section 118, the loop moves out of the opening of the engagement feature 230, thereby detaching the treatment device 200 from the delivery system 100. The force provided from the compressible section 118 during decompression can also push the implant 200 distally away from the distal end 104 of the delivery system 100, creating separation between the delivery system 100 and the treatment device 200.

FIG. 2 is an illustration of an example assembly at a proximal end of an intravascular delivery system 100 for providing strain relief at a distal end 154 of a pull wire 150 when the distal end 154 of the pull wire 150 is positioned to secure a treatment device 200 to the delivery system 100. The distal end 154 of the pull wire 150 can secure the treatment device 200 to the delivery system 100 as described in relation to FIG. 1 or by other means that can result in the treatment device 200 being deployed upon proximal movement of the pull wire 150.

The assembly at the proximal end of the delivery system 100 can include the pull wire 150, a delivery tube 110, an intermediate hypotube 130, and a sheath 170. The pull wire 150 can extend within the delivery tube 110, intermediate hypotube 130, and sheath 170. The intermediate hypotube 130 can be affixed to the delivery tube 110 and extend proximally from the delivery tube 110. The pull wire 150 need not be solidly connected to the intermediate hypotube 130, rather the proximal end of the pull wire 150 can be beaded such that a stretch relief gap 190 exists between the bead and the proximal end of the intermediate hypotube 130. The gap 190 can allow the proximal end of the pull wire 150 to move in relation to the proximal end 112 of the delivery tube 110 and intermediate hypotube 130 during tracking in tortuous anatomy, thereby minimizing the potential for premature retraction of the pull wire 150 at its distal end.

The pull wire 150 can have a bead, bump, extension, protrusion, or other feature (referred to herein generically as "bead") 156 at its proximal end 152 that extends in a radial direction beyond an outer circumference 158 of the pull wire 150 to a dimension that inhibits the bead 156 from entering the lumen 136 of the intermediate hypotube 130. The intermediate hypotube 130 can have a proximal end 132 that is positioned a gap distance 190 from the bead. The proximal end 132 of the intermediate hypotube 130 can be sized to maintain a position distal to the proximal end of the pull wire 150, so that if the gap 190 collapses during manipulation of the delivery system, the bead 156 is inhibited from entering the intermediate hypotube 130.

Alternatively, the intermediate hypotube 130 can include an alternative engagement feature, such as an obstruction in the lumen of the intermediate hypotube. In which case, the bead 156 can be sized to enter the lumen 136 of the intermediate hypotube 130, and the alternative engagement feature can prevent further distal movement of the bead 156 into the lumen 136. In such an example, the gap distance 190 can be understood to be the length through which the bead 156 can travel in the distal direction in relation to the proximal end 112 of the delivery tube 110 before becoming engaged to the alternative engagement feature.

The assembly can further include a sheath 170 to cover a proximal portion of the pull wire 150 extending out of the intermediate hypotube 132 to prevent inadvertent manipulation and/or breakage of the pull wire 150. The sheath 170 can be affixed to the intermediate hypotube section 130 with welds, glue, interference fit, or other means 178. The sheath 170 can have a lumen 176 sized to fit over an outer circumference of the proximal end 132 of the intermediate hypotube 130 and at least a portion of the intermediate hypotube 130. A surface within the lumen 176 of the sheath 170 can be detachably attached to an outer surface of the intermediate hypotube 130.

The intermediate hypotube 130 can be affixed to the delivery tube 110 with welds, glue, interference fit, or other means 124. The intermediate hypotube 130 can have an outer circumference sized to fit within the lumen of the delivery tube 110. An outer surface of the intermediate hypotube 130 can be affixed to an inner surface of the lumen 116 of the delivery tube 110 such that the intermediate hypotube 130 is not easily detached from the delivery tube 110 during a treatment procedure.

The intermediate hypotube 130 can have an extendable section 138 positioned within the lumen 116 of the delivery tube 110. The extendable section 138 can be stretched during a treatment procedure to elongate the intermediate hypotube 130. The intermediate hypotube 130 can be affixed to the delivery tube 110 at an attachment point 124 that is in the distal direction 14 in relation to the extendable section 138 such that when the extendable section 138 is stretched, the intermediate hypotube 130 extends further in the proximal direction 12 from the proximal end 112 of the delivery tube 110.

To prevent premature elongation of the intermediate hypotube 130, the intermediate hypotube can be attached with a breakable attachment 122 to the delivery tube 110 on a proximal side of the extendable section 138, near the proximal end 112 of the delivery tube 110.

The extendable section 138 can include areas of the intermediate hypotube 130 where sections have been cut or removed. By way of illustration, FIG. 2 shows the strain relief section 138 having a spiral cut in the hypotube 130.

The intermediate hypotube 130 can have a length that is significantly shorter than the length of the delivery tube 110. During a treatment, the proximal end 112 of the delivery tube 110 can be positioned outside of the patient while the distal end 114 of the delivery tube is positioned near a treatment site within the patient. While the delivery tube 110 is positioned as described, the proximal end 132 of the intermediate hypotube 130 can be positioned outside of the patient, and the intermediate hypotube 130 need not extend into the patient.

FIG. 3 illustrates positioning of an implant 200 such as an embolic coil suitable for aneurysm treatment, a guide catheter 300, and a delivery system 100 including a delivery tube 110 and pull wire 150 within tortuous vasculature (vasculature not illustrated). At bends A, B, and C, the delivery tube 110 can extend to a sidewall of the guide catheter 300 on each outer curve of each bend, and likewise, the pull wire 150 can extend to a sidewall of the delivery tube 110 on each outer curve of each bend. During a procedure, the delivery tube 110 and pull wire 150 can be fed into the guide catheter 300 in the distal direction, first passing through bend A, then bend B, and then bend C. As the delivery tube 110 and pull wire 150 navigate the bends, the proximal end 152 of the pull wire 150 can progressively approach the proximal end 132 of the intermediate hypotube 130, such that the pull wire 150 proximal end 152 moves in the distal direction 14 in relation to the delivery tube 110.

Figure 4A:
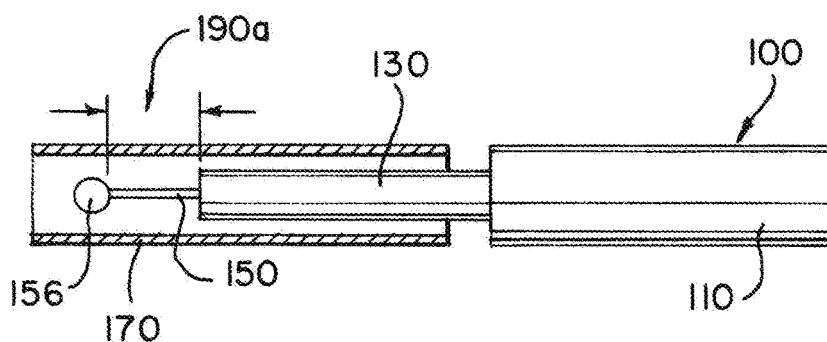
FIGS. 4A through 4D are illustrations of a proximal assembly of an intravascular delivery system such as illustrated in FIG. 2 when the delivery system is navigated through turns in a body lumen such as illustrated in FIG. 3 according to aspects of the present invention.
Figure 4B:
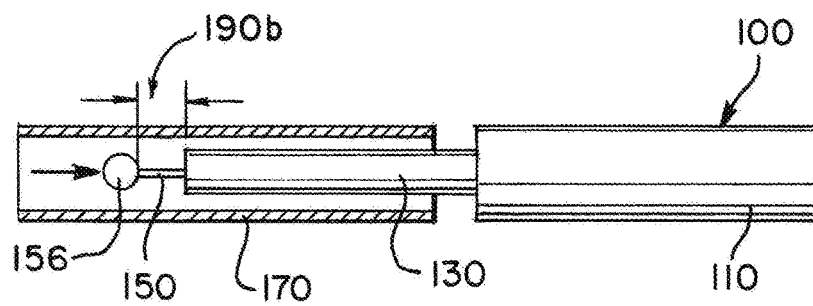
Figure 4C:
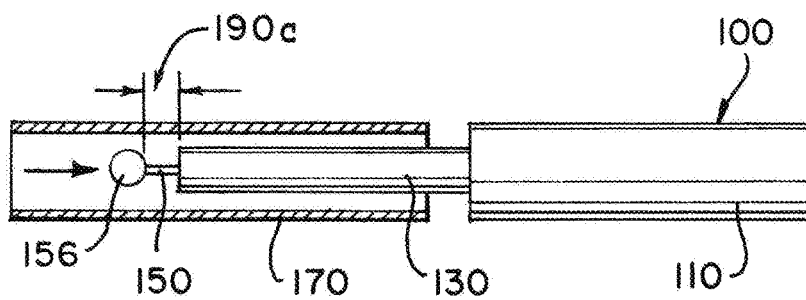
Figure 4D:
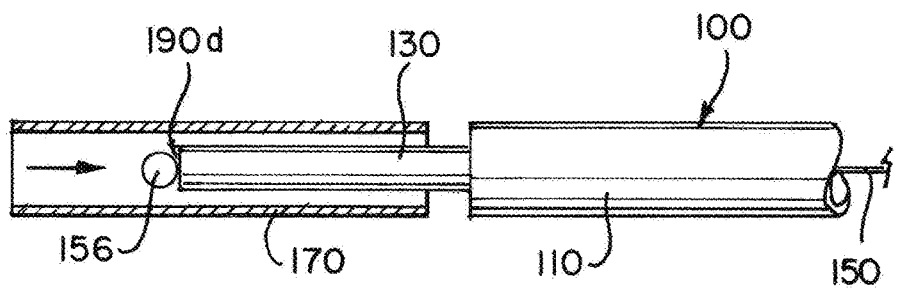

FIGS. 4A through 4D illustrate the progressive movement of the proximal end 152 of the pull wire 150 as the delivery system 100 moves distally through bends A, B, and C. FIG. 4A illustrates the positioning of the proximal end 152 of the pull wire 150 as the distal end 104 of the delivery system 100 approaches bend A. FIG. 4B illustrates the movement of the proximal end 152 of the pull wire 150 toward the intermediate hypotube 130 as the distal end 104 of the delivery system 100 rounds bend A and approaches bend B. FIG. 4C illustrates the proximal end of the pull wire 150 moving further toward the intermediate hypotube 130 as the distal end 104 of the delivery system 100 rounds bend B and approaches bend C. FIG. 4D illustrates the bead on the proximal end of the pull wire 150 making contact with the proximal end of the intermediate hypotube 130 as the distal end 104 of the delivery system 100 rounds bend C and approaches a treatment site.

Referring collectively to the illustrations in FIGS. 3 and 4A through 4D, as the delivery system 100 is moved distally to a treatment site, the proximal end 152 of the pull wire 150 can be free to move in the proximal and distal directions in relation to the delivery tube 110 and intermediate hypotube 130. As illustrated, the bead 156 on the pull wire 150 can approach the proximal end of the hypotube 130 as the delivery system 100 is moved distally to a treatment site. Arrows illustrated in FIGS. 4B through 4D indicate the distal movement of the proximal end 152 of the pull wire 150.

A gap 190a, 190b, 190c, 190d between the bead 156 and the engagement surface 132 of the intermediate hypotube can become progressive smaller as illustrated in FIGS. 4A through 4D as the delivery system 100 is moved distally. In FIG. 4D the bead 156 is illustrated engaged to the intermediate hypotube 130. In this position, the proximal end 152 of the pull wire 150 is inhibited from moving further in the distal direction 14 and the gap 190d spacing is collapsed, essentially measuring zero.

Referring to FIG. 2, the delivery system 100 can include a gap spacing 190 that is measurable between a distal surface of the bead 156 and the engagement surface 132 of the intermediate hypotube 130 when the delivery system 100 is elongated in an essentially linear configuration from end to end. The gap spacing 190 can be sized such that the bead 156 is unlikely to engage the hypotube 130 as the delivery system 100 is delivered to a treatment site. A larger gap spacing can allow for a greater distance of travel of the proximal end 152 of the pull wire 150, allowing for greater strain relief at the distal end of the pull wire, thereby reducing the likelihood of premature deployment of a treatment device. The maximum length of the gap spacing 190 can be limited by ease of manipulation of the proximal end of the delivery system 100. For example, it may be difficult for a physician to manipulate a delivery system having a proximal assembly such as illustrated in FIG. 2 that is several inches long. The gap 190 can therefore be sized to sufficiently relieve strain on the distal end of the pull wire 150 to sufficiently reduce the likelihood of premature deployment of a treatment device and also to facilitate ease of manipulation of the delivery system during a treatment procedure.

FIGS. 5A and 5B illustrate the manipulation of the assembly at the proximal end of the delivery system 100 to deploy a treatment device (e.g. implant). FIG. 5C illustrates the movement of the distal end 154 of the pull wire 150 to disengage the implant 200 in response to the manipulation of the proximal end of the delivery system illustrated in FIGS. 5A and 5B.

FIG. 5A illustrates the sheath 170 covering a proximal portion of the pull wire 150 including the proximal end 152 and bead 156, the sheath 170 affixed to the intermediate hypotube 130 with welds 178, the intermediate hypotube being affixed to the delivery tube 110 with distal welds 124, and the intermediate hypotube 130 also secured to the delivery tube at the proximal end of the delivery tube 100 with proximal welds 122. The proximal welds 122 can be designed to be broken by a user during a treatment, while the other welds 178, 124 affixing the intermediate hypotube 120 to the sheath 170 and delivery tube 110 can be designed to remain securely attached when the assembly is manipulated during a treatment.

FIG. 5B illustrates the sheath 170 being pulled proximally as indicated by the arrow. During a treatment, a user can apply a force F sufficient to break the proximal welds 122 to detach the proximal end 112 of the delivery tube 110 from the intermediate hypotube 130. Alternatively, the proximal welds 128 can be broken with a twisting or bending force. After welds 128 are broken, the sheath 170 can be moved proximally as indicated by the arrow. The extendable section 138 of the intermediate hypotube 130 can expand, allowing the intermediate hypotube 130 to further extend out of the proximal end 112 of the delivery tube 110. As the sheath 170 is moved proximally and the intermediate hypotube 130 is extended, the intermediate hypotube 130 can engage the bead 156 on the pull wire 150. As the sheath 170 is further moved proximally and the intermediate hypotube 130 is further extended, the bead 156 can be moved proximally, causing the length of the pull wire 150 to move proximally.

FIG. 5C illustrates the distal end 154 of the pull wire 150 extended through the loop wire 140. The arrow indicates proximal movement of the distal end 154 of the pull wire 150 in response to the bead 156 on the pull wire 150 being moved proximally as illustrated in FIG. 5B. The bead 156 can be moved proximally through a distance sufficient to cause the distal end 154 of the pull wire to pass proximally through the loop wire 140, thereby disengaging the loop wire 140. Once the loop wire 140 is disengaged, the implant 100 can deploy.

FIG. 6 is a flow chart outlining example method steps for designing and/or constructing a delivery system according to the present invention. FIG. 7 is a flow chart outlining example method steps for treating a patient using a delivery system according to the present invention. For each method 600, 700, the method steps can be implemented by the example delivery systems and means described herein or by means that would be known to one of ordinary skill in the art. Method steps are generally presented in an order in which they can be preferably performed. Certain steps can be performed simultaneously or in alternative order as would be appreciated and understood by one of ordinary skill in the art.

Referring to the method 600 outlined in FIG. 6, in step 610 a delivery tube, intermediate hypotube, and pull wire can be provided. The provided components can be the delivery tube 110, intermediate hypotube 130, and pull wire 150 described herein, a variation thereof, or an equivalent component as would be known to one skilled in the art.

In step 620, an engagement bump can be formed near the proximal end of the pull wire, and the engagement bump can be sized larger than lumen of the intermediate hypotube such that the engagement bump inhibits the proximal end of the pull wire from entering the lumen of the intermediate hypotube. The engagement bump can be a bead 156 on the pull wire 150 as described herein, a variation thereof, or an equivalent component as would be known to one skilled in the art.

In step 630, the intermediate hypotube can be affixed to the delivery tube such that the intermediate hypotube extends proximally from the delivery tube and is stretchable to further extend proximally from the proximal end of the delivery tube. The intermediate hypotube can be affixed at the distal attachment location 124 as illustrated herein, otherwise attached as described herein, and/or attached by other means as would be known to one skilled in the art. The intermediate hypotube can be stretchable along a portion 138 of its length as illustrated herein, otherwise stretchable as described herein, and/or extendable by other means as would be known to one skilled in the art.

In step 640, the pull wire can be positioned such that the wire extends through the lumens of the intermediate hypotube and delivery tube, the pull wire extends proximally from the lumen of the intermediate hypotube, and the engagement bump is positioned in the proximal direction in relation to the intermediate hypotube.

In step 650, an intravascular treatment device can be secured with a distal portion of the pull wire at a distal end of the delivery tube. The intravascular treatment device can be an embolic coil 200 as illustrated herein, another treatment device as described herein, or a treatment device that would be known to one skilled in the art. The distal portion of the pull wire can form part of an assembly that can secure the treatment device when the treatment device is being delivered and deploy the treatment device with a proximal movement of the distal portion of the pull wire in relation to the treatment device and/or distal end of the delivery tube. The assembly to deploy the treatment device can be a mechanical assembly such as illustrated and/or described herein, or an assembly as would be known to one skilled in the art.

In step 660, the pull wire can be positioned such that the distal end of the pull wire is fixed in relation to the distal end of the delivery tube and the proximal end of the pull wire is slidably translatable in relation to the proximal end of the delivery tube. The distal end of the pull wire can be fixed in relation to the distal end of the delivery tube by virtue of forming part of an assembly that secures the treatment device when the treatment device is being delivered to the treatment site. The portion of the pull wire forming the assembly to secure the treatment device can be the sole attachment point between the pull wire such that a majority of the length of the pull wire has freedom of movement within the confines of the delivery tube, and the proximal end of the pull wire is free to move in the distal direction and proximal direction in relation to the proximal end of the delivery tube.

In step 670, a sheath can be affixed to the intermediate hypotube. The sheath can be positioned to surround the proximal end of the pull wire. The sheath can be a sheath 170 as illustrated and described herein, a variation thereof, or an equivalent component as would be known to one skilled in the art. The sheath can be attached to the intermediate hypotube at locations 178 as illustrated herein, otherwise attached as described herein, and/or attached by other means as would be known to one skilled in the art. The sheath can be shaped to be grasped by a physician during a treatment.

Referring to the method 700 outlined in FIG. 7, in step 710 an intravascular delivery system having a delivery tube, intermediate hypotube, and pull wire can be selected. The intravascular delivery system can be an example delivery system 100 described herein, a variation thereof, or an equivalent system as would be known to one skilled in the art.

In step 720, the proximal end of the pull wire can be surrounded by a sheath. The sheath can be a sheath 170 as illustrated and described herein, a variation thereof, or an equivalent component as would be known to one skilled in the art. The proximal end of the pull wire can be surrounded by the sheath in step 720 by virtue of the selected intravascular delivery system (step 710) including the sheath positioned to surround the proximal end of the pull wire. Alternatively, the sheath can be an ancillary component selected separately from the intravascular delivery system, and the sheath can be positioned to surround the proximal end of the pull wire in step 720. In either case, the sheath, when attached, can serve to protect the proximal end of the pull wire from inadvertent manipulation and/or breakage.

In step 730, the delivery system can be extended through vasculature of a patient.

In step 740, the proximal end of the pull wire can be allowed to move distally in relation to the proximal end of the delivery tube as the delivery system is extended through vasculature of the patient.

In step 750, the proximal end of the pull wire can be inhibited from entering the intermediate hypotube and delivery tube by engaging a bead on the pull wire to the hypotube.

In step 760, the sheath can be moved to elongate the intermediate hypotube.

In step 770, the proximal end of the pull wire can be engaged and moved by elongating the intermediate hypotube.

In step 780, a treatment device can be deployed by moving the proximal end of the pull wire proximally in relation to the proximal end of the delivery tube.

The descriptions contained herein are examples of embodiments of the invention and are not intended in any way to limit the scope of the invention. As described herein, the invention contemplates many variations and modifications of the intravascular delivery system, including alternative components, alternative features to prevent the proximal end of the pull wire from becoming inaccessible due to distal movement of the pull wire, alternative features to protect the proximal end of the pull wire from inadvertent, premature manipulation, alternative means for extending the intermediate hypotube from the proximal end of the delivery tube, etc. These modifications would be apparent to those having ordinary skill in the art to which this invention relates and are intended to be within the scope of the claims which follow.

What is claimed is:

1. An intravascular delivery system comprising:
   a delivery tube sized to be delivered through a patient to a treatment site;
   an intermediate hypotube comprising an expandable section, the intermediate hypotube affixed to the delivery tube and extending in a proximal direction from a proximal end of the delivery tube; and
   a pull wire extending through a lumen of the intermediate hypotube and through a lumen of the delivery tube,
   wherein the pull wire comprises an engagement bump affixed thereto and positioned in the proximal direction in relation to a proximal end of the hypotube,
   wherein the engagement bump is sized to inhibit movement of the engagement bump into the lumen of the intermediate hypotube,
   wherein a distal end of the intermediate hypotube is affixed to a lumen of the delivery tube,
   wherein the expandable section of the intermediate hypotube is positioned within the lumen of the delivery tube,
   wherein the distal end of the intermediate hypotube is in a distal direction relative to the expandable section, and
   wherein a proximal portion of the intermediate hypotube is detachably attached to the delivery tube and is in a proximal direction relative to the expandable section.

2. The intravascular delivery system of claim 1, further comprising:
   a sheath attached to the intermediate hypotube,
   wherein a proximal portion of the pull wire comprising the engagement bump is positioned within a lumen of the sheath.

3. The intravascular delivery system of claim 1, wherein the engagement bump is movable in a distal direction in relation to the proximal end of the intermediate hypotube.

4. The intravascular delivery system of claim 3, further comprising:
   a stretch relief gap defining a length of movement of the engagement bump in a distal direction in relation to the intermediate hypotube through which the engagement bump is unengaged to the intermediate hypotube.

5. The intravascular delivery system of claim 1,
   wherein an intravascular treatment device is positioned approximate a distal end of the intravascular delivery system, and
   wherein the pull wire is movable to deploy the intravascular treatment device.

6. A method comprising:
   providing a delivery tube sized to be delivered through a patient to a treatment site and comprising a lumen therethrough;
   providing an intermediate hypotube comprising a lumen therethrough;
   providing a pull wire;
   forming an engagement bump on the pull wire approximate a proximal end of the pull wire;
   affixing the intermediate hypotube to the delivery tube such that the intermediate hypotube extends in a proximal direction from a proximal end of the delivery tube and the intermediate hypotube is stretchable to further extend from the proximal end of the delivery tube;
   positioning the pull wire to extend through the lumen of the delivery tube and through the lumen of the intermediate hypotube;
   positioning the engagement bump in the proximal direction in relation to a proximal end of the intermediate hypotube; and
   sizing the engagement bump to inhibit movement of the engagement bump into the lumen of the intermediate hypotube,
   wherein the step of affixing the intermediate hypotube to the delivery tube further comprises:
   affixing a distal end of the intermediate hypotube within the lumen of the delivery tube;
   providing a strain relief section on the intermediate hypotube;
   positioning the strain relief section of the intermediate hypotube within the lumen of the delivery tube such that the distal end is in a distal direction relative to the strain relief section; and
   detachably attaching a proximal portion of the intermediate hypotube to the delivery tube, wherein the proximal portion is in a proximal direction relative to the strain relief section.

7. The method of claim 6, further comprising:
   positioning the pull wire such that a distal end of the pull wire is fixed in relation to a distal end of the delivery tube and the proximal end of the pull wire is slidably translatable in relation to the proximal end of the delivery tube.

8. The method of claim 6, further comprising:
providing a sheath comprising a lumen therethrough;
affixing the sheath to the intermediate hypotube; and
positioning the engagement bump within the lumen of the sheath.

9. The method of claim 6, further comprising:
providing a stretch relief gap such that the stretch relief gap defines a length of movement of the engagement bump in a distal direction in relation to the intermediate hypotube through which the engagement bump is unengaged to the intermediate hypotube.

10. The method of claim 6, further comprising:
positioning a distal end of the pull wire to secure an intravascular treatment device approximate a distal end of the delivery tube.

11. A method for deploying an intravascular treatment device, the method comprising:
selecting an intravascular delivery system comprising a delivery tube, an intermediate hypotube extending from a proximal end of the delivery tube, and a pull wire extending through a lumen of the delivery tube and a lumen of the intermediate hypotube;
extending the intravascular delivery system through vasculature of a patient;
allowing a proximal end of the pull wire to move in a distal direction in relation to the proximal end of the delivery tube as the intravascular delivery system is extended through the vasculature of the patient;
surrounding the proximal end of the pull wire with a sheath; and
deploying the intravascular treatment device by moving the proximal end of the pull wire in a proximal direction in relation to the proximal end of the delivery tube,
wherein the step of deploying the intravascular treatment device further comprises:
moving the sheath in the proximal direction in relation to the delivery tube to thereby elongate the intermediate hypotube,
engaging the proximal end of the pull wire to the intermediate hypotube, and
moving the proximal end of the pull wire in the proximal direction in relation to the proximal end of the delivery tube by elongating the intermediate hypotube while the proximal end of the pull wire is engaged to the intermediate hypotube.

12. The method of claim 11, further comprising:
engaging a bead positioned approximate the proximal end of the pull wire to a proximal end of the intermediate hypotube, thereby inhibiting the proximal end of the pull wire from entering the lumen of the intermediate hypotube.

* * * * *